(12) United States Patent
Hsieh et al.

(10) Patent No.: US 8,349,316 B2
(45) Date of Patent: Jan. 8, 2013

(54) LACTOBACILLUS FERMENTUM SG-A95 FOR IMPROVING ORAL BACTERIAL GROUPS AND HEALTH CARE COMPOSITIONS THEREOF

(75) Inventors: Chu Yang Hsieh, Tainan (TW); Yu Shan Wei, Tainan (TW); Chi Chiang Yang, Taichung (TW)

(73) Assignee: Syngen Biotech, Co., Ltd., Hsin-Ying Tainan (TW)

( * ) Notice: Subject to any disclaimer, the term of this patent is extended or adjusted under 35 U.S.C. 154(b) by 147 days.

(21) Appl. No.: 12/900,905

(22) Filed: Oct. 8, 2010

(65) Prior Publication Data
US 2011/0262372 A1   Oct. 27, 2011

(30) Foreign Application Priority Data
Apr. 27, 2010 (TW) ............................... 99113257 A (51) Int. Cl.
*A01N 63/00* (2006.01)
(52) U.S. Cl. .................................... 424/93.45

(58) Field of Classification Search .................. None
See application file for complete search history.

(56) References Cited

U.S. PATENT DOCUMENTS

| | | | | |
|---|---|---|---|---|
| 4,746,512 | A | * | 5/1988 | Kawai et al. ............... 424/203.1 |
| 2006/0067921 | A1 | * | 3/2006 | Conway ..................... 424/93.45 |
| 2006/0093592 | A1 | * | 5/2006 | Cheruvanky et al. ...... 424/93.45 |

OTHER PUBLICATIONS

Koll-Klais et al., Oral Microbiology and Immunology, 2005, vol. 25, pp. 354-361.*

* cited by examiner

*Primary Examiner* — Allison Ford
*Assistant Examiner* — Yvonne Pyla
(74) *Attorney, Agent, or Firm* — WPAT, P.C.; Anthony King (57) ABSTRACT

The present invention provides a strain of *Lactobacillus fermentum* SG-A95 with deposit number of CGMCC NO. 3248 and a fermentation product thereof. The present invention also provides a health care composition for improving oral bacteria population, which comprises the *Lactobacillus fermentum* SG-A95 or the fermentation product thereof.

8 Claims, 4 Drawing Sheets

```
Query    5    GTGC-GAGTGCTATACATGCAAGTCGAACGCGTTGGCCCAATTGATTGATGGTGCTTGCA    63
              ||||  |||||||||||||||||||||||||||||||||||||||||||||||||||||
Sbjct    4    GTGCGGTGTGCTATACATGCAAGTCGAACGCGTTGGCCCAATTGATTGATGGTGCTTGCA    63

Query    64   CCTGATTGATTTTGGTCGCCAACGAGTGGCGGACGGGTGAGTAACACGTAGGTAACCTGC   123
              ||||||||||||||||||||||||||||||||||||||||||||||||||||||||||||
Sbjct    64   CCTGATTGATTTTGGTCGCCAACGAGTGGCGGACGGGTGAGTAACACGTAGGTAACCTGC   123

Query    124  CCAGAAGCGGGGGACAACATTTGGAAACAGATGCTAATACCGCATAACAGCGTTGTTCGC   183
              ||||||||||||||||||||||||||||||||||||||||||||||||||||||||||||
Sbjct    124  CCAGAAGCGGGGGACAACATTTGGAAACAGATGCTAATACCGCATAACAGCGTTGTTCGC   183

Query    184  ATGAACAACGCTTAAAAGATGGCTTCTCGCTATCACTTCTGGATGGACCTGCGGTGCATT   243
              ||||||||||||||||||||||||||||||||||||||||||||||||||||||||||||
Sbjct    184  ATGAACAACGCTTAAAAGATGGCTTCTCGCTATCACTTCTGGATGGACCTGCGGTGCATT   243

Query    244  AGCTTGTTGGTGGGGTAACGGCCTACCAAGGCGATGATGCATAGCCGAGTTGAGAGACTG   303
              ||||||||||||||||||||||||||||||||||||||||||||||||||||||||||||
Sbjct    244  AGCTTGTTGGTGGGGTAACGGCCTACCAAGGCGATGATGCATAGCCGAGTTGAGAGACTG   303

Query    304  ATCGGCCACAATGGGACTGAGACACGGCCCATACTCCTACGGGAGGCAGCAGTAGGGAAT   363
              ||||||||||||||||||||||||||||||||||||||||||||||||||||||||||||
Sbjct    304  ATCGGCCACAATGGGACTGAGACACGGCCCATACTCCTACGGGAGGCAGCAGTAGGGAAT   363

Query    364  CTTCCACAATGGGCGCAAGCCTGATGGAGCAACACCGCGTGAGTGAAGAAGGGTTTCGGC   423
              ||||||||||||||||||||||||||||||||||||||||||||||||||||||||||||
Sbjct    364  CTTCCACAATGGGCGCAAGCCTGATGGAGCAACACCGCGTGAGTGAAGAAGGGTTTCGGC   423

Query    424  TCGTAAAGCTCTGTTGTTAAAGAAGAACACGTATGAGAGTAACTGTTCATACGTTGACGG   483
              ||||||||||||||||||||||||||||||||||||||||||||||||||||||||||||
Sbjct    424  TCGTAAAGCTCTGTTGTTAAAGAAGAACACGTATGAGAGTAACTGTTCATACGTTGACGG   483

Query    484  TATTTAACCAGAAAGTCACGGCTAACTACGTGCCAGCAGCCGCGGTAATACGTAGGTGGC   543
              ||||||||||||||||||||||||||||||||||||||||||||||||||||||||||||
Sbjct    484  TATTTAACCAGAAAGTCACGGCTAACTACGTGCCAGCAGCCGCGGTAATACGTAGGTGGC   543

Query    544  AAGCGTTATCCGGATTTATTGGGCGTAAAGAGAGTGCAGGCGGTTTTCTAAGTCTGATGT   603
              ||||||||||||||||||||||||||||||||||||||||||||||||||||||||||||
Sbjct    544  AAGCGTTATCCGGATTTATTGGGCGTAAAGAGAGTGCAGGCGGTTTTCTAAGTCTGATGT   603

Query    604  GAAAGCCTTCGGCTTAACCGGAGAAGTGCATCGGAAACTGGATAACTTGAGTGCAGAAGA   663
              ||||||||||||||||||||||||||||||||||||||||||||||||||||||||||||
Sbjct    604  GAAAGCCTTCGGCTTAACCGGAGAAGTGCATCGGAAACTGGATAACTTGAGTGCAGAAGA   663

Query    664  GGGTAGTGGAACTCCATGTGTAGCGGTGGAATGCGTAGATATATGGAAGAACACCAGTGG   723
              ||||||||||||||||||||||||||||||||||||||||||||||||||||||||||||
Sbjct    664  GGGTAGTGGAACTCCATGTGTAGCGGTGGAATGCGTAGATATATGGAAGAACACCAGTGG   723

Query    724  CGAAGGCGGCTACCTGGTCTGCAACTGACGCTGAGACTCGAAAGCATGGGTAGCGAACAG   783
              ||||||||||||||||||||||||||||||||||||||||||||||||||||||||||||
Sbjct    724  CGAAGGCGGCTACCTGGTCTGCAACTGACGCTGAGACTCGAAAGCATGGGTAGCGAACAG   783
```

FIG. 1A

```
Query  784   GATTAGATACCCTGGTAGTCCATGCCGTAAACGATGAGTGCTAGGTGTTGGAGGGTTTCC  843
             ||||||||||||||||||||||||||||||||||||||||||||||||||||||||||||
Sbjct  784   GATTAGATACCCTGGTAGTCCATGCCGTAAACGATGAGTGCTAGGTGTTGGAGGGTTTCC  843

Query  844   GCCCTTCAGTGCCCGGAGCTAACGCATTAAGCACTCCGCCTGGGGAGTACGACCGCAAGG  903
             |||||||||||||| |||||||||||||||||||||||||||||||||||||||||||||
Sbjct  844   GCCCTTCAGTGCC-GGAGCTAACGCATTAAGCACTCCGCCTGGGGAGTACGACCGCAAGG  902

Query  904   TTGAAACTCAAAGGAATTGACGGGG-CCCGCACAAGCGGTGGAGCATGTGGTTTAATTCG  962
             |||||||||||||||||||||||| ||||||||||||||||||||||||||||||||||
Sbjct  903   TTGAAACTCAAAGGAATTGACGGGGGCCCGCACAAGCGGTGGAGCATGTGGTTTAATTCG  962

Query  963   AAGCTACGCGA-GA-CCTTACCAG-TCT-GACATCTTGCGC-AACCCTAGAGATAGGGCG  1017
             |||||||||| || ||||||||| ||| |||||||||||| ||||||||||||||||||
Sbjct  963   AAGCTACGCGAAGAACCTTACCAGGTCTTGACATCTTGCGCAACCCTAGAGATAGGGCG  1022

Query  1018  TT-CCTTCGGGA-CGCA-TGACAG-TG-TGCATGGTCGTCGTCAGCTCGTGTCGTGAGAT  1072
             || |||||||| |||| |||||| || |||||||||||||||||||||||||||||||||
Sbjct  1023  TTTCCTTCGGGAACGCAATGACAGGTGGTGCATGGTCGTCGTCAGCTCGTGTCGTGAGAT  1082

Query  1073  GTTGGGTTA-GTCCCGCAACGAGCGCACCCCTCGTTTACTAG     1113
             |||||||| |||||||||||||||| |||  ||| ||||||
Sbjct  1083  GTTGGGTTAAGTCCCGCAACGAGCGCAACCCTTGTT-ACTAG     1123
```

LACTOBACILLUS FERMENTUM SG-A95 FOR IMPROVING ORAL BACTERIAL GROUPS AND HEALTH CARE COMPOSITIONS THEREOF

FIELD OF THE INVENTION

The present invention relates to a *Lactobacillus fermentum* strain SG-A95 for inhibiting bacterial growth in oral, improving oral bacterial groups and fermentation product thereof.

BACKGROUND OF THE INVENTION

Normal human mouth contains lots of bacteria, fungi, and even viruses, where bacteria are the major population. There are 100 million bacteria in one milliliter of saliva, and the whole mouth contains more than 600 kinds of bacteria. Not all of these bacteria are pathogens. Certain probiotics are also present. These bacteria maintain a relative balance and are non-pathogenic under normal condition. Under the situation of low immunity or resistance, oral environmental changes, medication, or systematic disease, over growth of pathogens result in oral diseases, as minor as bad breath, dental plaque, gingivitis or as severe as cavity, periodontal disease and even bacteremia caused by massive bacteria reproduction after blood vessels infection.

According to the yearly National Health Insurance statistic analysis by Taiwan Dental Association, 90% adults in Taiwan area suffering periodontal diseases demonstrated the importance of oral hygiene.

There are two kinds of periodontal diseases, i.e., gingivitis and periodontitis. The major symptoms of gingivitis are gum bleeding, swelling, redness and etc. Periodontitis indicates the status of destroyed alveolar bone which supports gum tissue and teeth.

One of the periodontal disease symptoms is deepen grove between teeth and gum resulting in periodontal pocket. The periodontal pocket of people with healthy teeth is around 1 to 2 mm, which is 3 to 4 mm of mild periodontal disease patients, 4 to 6 mm of moderate patients, and over 6 mm of severe patients. Along with deeper periodontal pocket, the gum is getting shorter. The appearance of longer or mobile teeth could be the warning sign of severe periodontal diseases. Gingivitis and periodontitis are caused by periodontal bacteria infection. The representative bacterium is *Porphyromonas gingivalis*.

Glycoprotein of saliva forms a film on the teeth surface which enables bacteria attachment. After bacteria utilizing the sugar of food, the film is getting bigger and thicker resulting in dental plaque. Moreover, if the dental plaque is formed in periodontal pocket, periodontal bacteria will reproduce massively in the dental plaque. Due to anaerobic characteristics of periodontal bacteria, the oxygen unreachable periodontal pocket is their most optimal growth condition. Dental plaque is also the incubator of *Streptococcus mutans*. More than 90% adults carry this type of bacteria in their mouth, which is also the major bacteria strain causing cavity. When acidic substances generated from sugar degradation by *Streptococcus mutans* erode enamel and dentin, it will cause cavity.

Periodontal bacteria invading gum will cause immunological reactions. Periodontal bacteria secret enzymes dissolving gum cell and invading the internal side of the gum. With minimal level of periodontal bacteria, the invasion can be stopped. As long as massive reproduction is established, the situation can not be controlled.

There are some present methods to prevent the formation of cavity or periodontal diseases, such as applying anti-adhesives to avoid bacteria attachment on teeth surface, and to minimize dental plaque formation, and bacteria erosion of dentin (R.O.C. patent application number 094144377); applying anti-bacterial reagent to inhibit bacteria growth (U.S. Pat. No. 5,368,845; WO 92/14475); or widely used fluoride to reduce the solubility of enamel against acidic substances for cavity prevention. However, studies of *Lactobacillus fermentum* and its oral disease curative effects are rarely seen.

SUMMARY OF THE INVENTION

The present invention discloses a strain of *Lactobacillus fermentum* SG-A95 with deposit number of CGMCC NO. 3248 and a fermentation product thereof.

The present invention also discloses a health composition for improving oral bacteria population, which comprises the *Lactobacillus fermentum* SG-A95 or the fermentation product thereof.

DETAILED DESCRIPTION OF THE INVENTION

The present invention provides a strain of *Lactobacillus fermentum* SG-A95 (deposit number CGMCC NO. 3248). CGMCC (China General Microbiological Culture Collection Center) which belongs to International Depository Authority (IDA) under the Budapest Treaty is located at Institute of Microbiology Chinese Academy of Sciences, No. 1 West Beichen Road, Chaoyang District, Beijing, China. The deposit of SG-A95 (Lactobacillus fermentum) (CGMCC NO. 3248) was received on Aug. 21, 2009 and the viability of the deposited microorganism was tested on Aug. 24, 2009 and was tested to be viable. The present invention further reveals that the *Lactobacillus fermentum* SG-A95 comprises codons as nucleotide sequences shown in SEQ ID NO:1. The present invention also reveals the fermentation product of medium cultured *Lactobacillus fermentum* SG-A95.

The present invention also provides a health care composition to improve oral bacteria population, wherein application of said *Lactobacillus fermentum* SG-A95 or its fermentation product on oral hygiene can effectively inhibit the growth of oral periodontal bacteria.

Figure 1A:
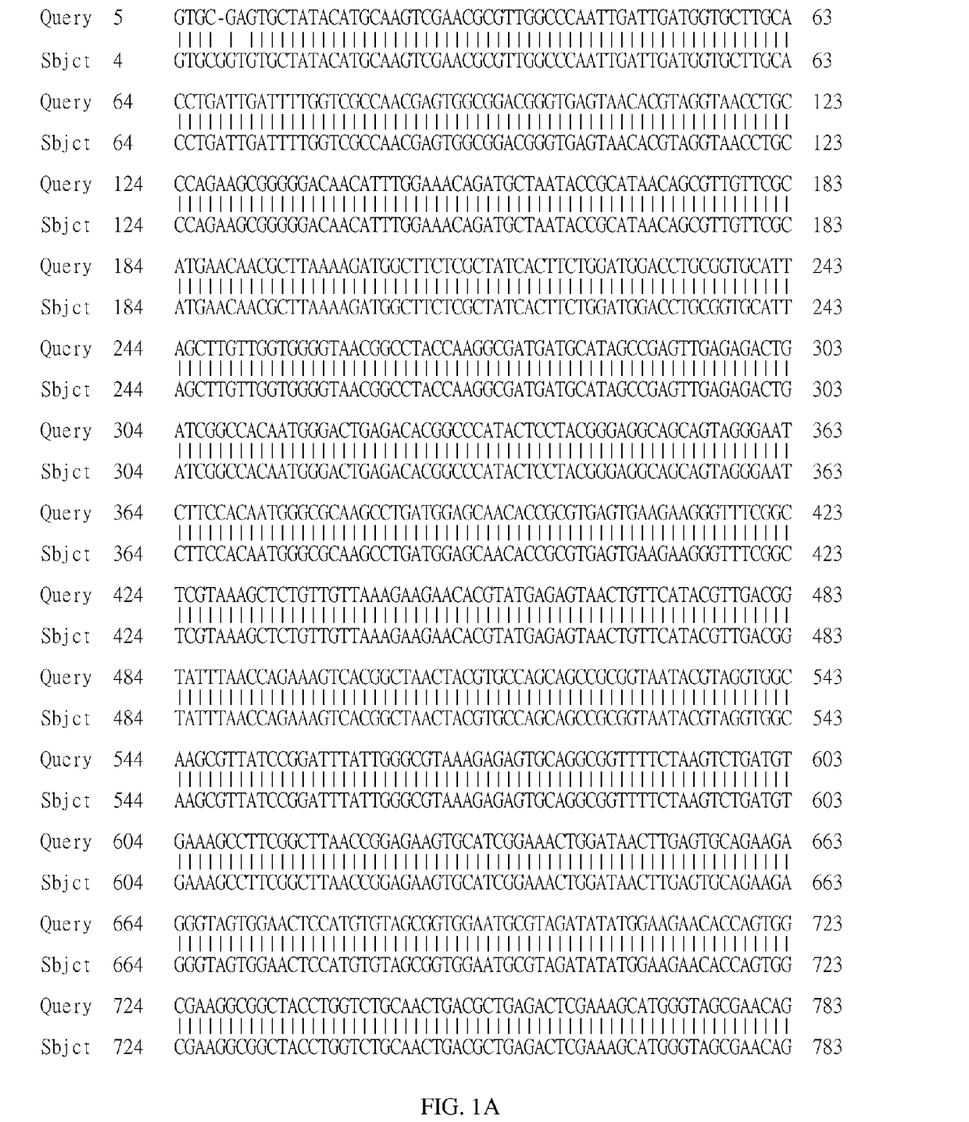
FIG. 1A and FIG. 1B show nucleotide sequence comparison of SEQ ID NO: 1 of the present invention and known *Lactobacillus fermentum* (bacterial strain ATCC14931 in US patent publication No. 2002/0094328) using NCBI blast program. Query sequence is from ATCC14931, and Sbjct sequence is SEQ ID NO: 1 of the present invention.
Figure 1B:
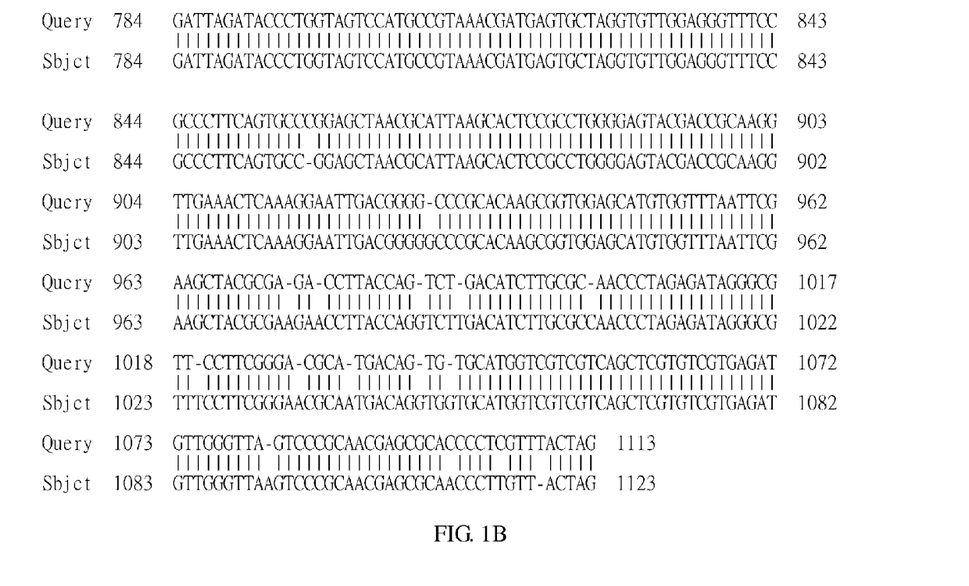
Figure 2:
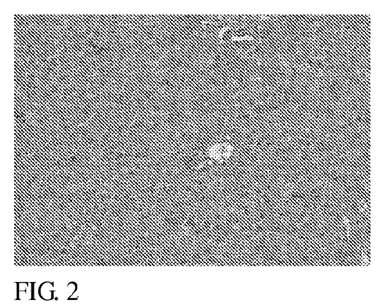
FIG. 2 shows liver tissue section of *Lactobacillus fermentum* SG-A95 treatment group (tLFP4) (200×).
Figure 3:
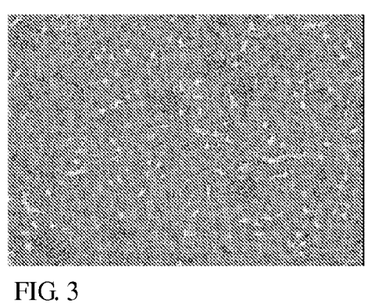
FIG. 3 shows kidney tissue section of *Lactobacillus fermentum* SG-A95 treatment group (tLFP4) (200×).
Figure 4:
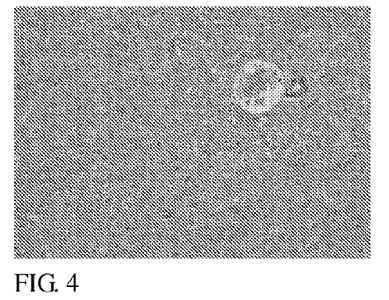
FIG. 4 shows liver tissue section of *Lactobacillus fermentum* SG-A95 treatment group (tLFBH) (200×).
Figure 5:
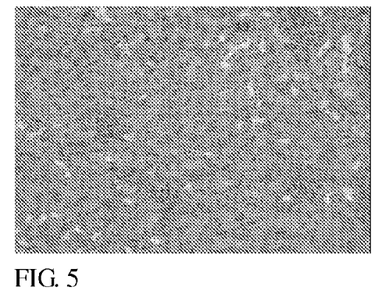
FIG. 5 shows kidney tissue section of *Lactobacillus fermentum* SG-A95 treatment group (tLFBH) (200×).
Figure 6:
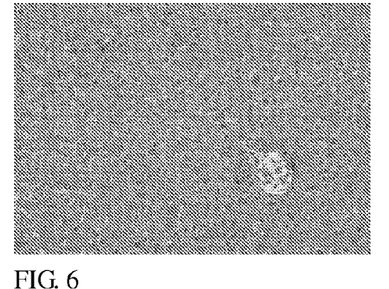
FIG. 6 shows liver tissue section of control group with tetracycline treatment (tTC) (200×).
Figure 7:
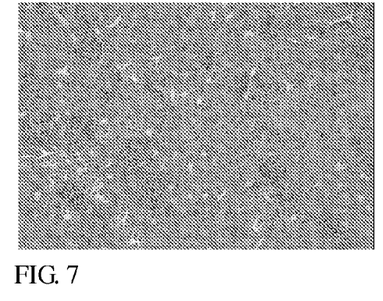
FIG. 7 shows kidney tissue section of control group with tetracycline treatment (tTC) (200×).
Figure 8:
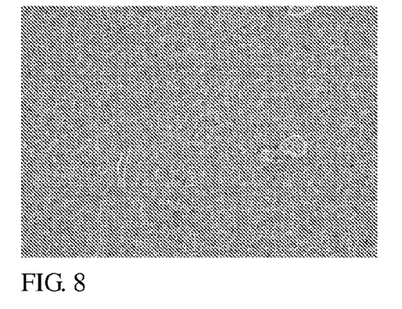
FIG. 8 shows liver tissue section of control group with no treatment (distilled water) (tMT) (200×).
Figure 9:
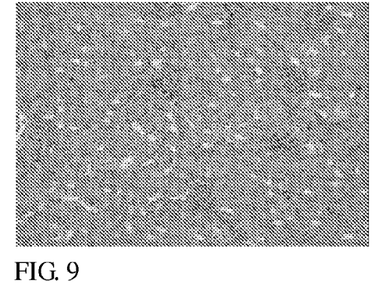
FIG. 9 shows kidney tissue section of control group with no treatment (distilled water) (tMT) (200×).
Figure 10:
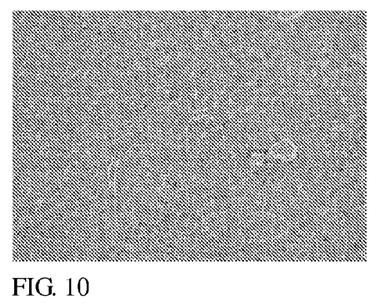
FIG. 10 shows liver tissue section of *Lactobacillus fermentum* SG-A95 prevention group (pLFP4) (200×).
Figure 11:
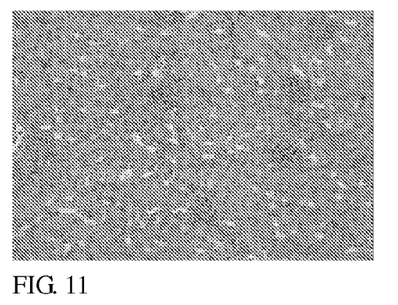
FIG. 11 shows kidney tissue section of *Lactobacillus fermentum* SG-A95 prevention group (pLFP4) (200×).
Figure 12:
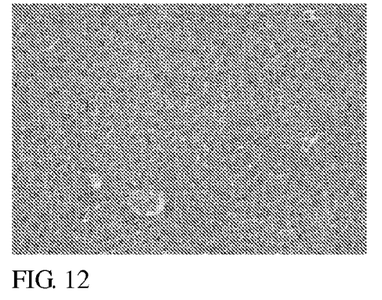
FIG. 12 shows liver tissue section of *Lactobacillus fermentum* SG-A95 prevention group (pLFBH) (200×).
Figure 13:
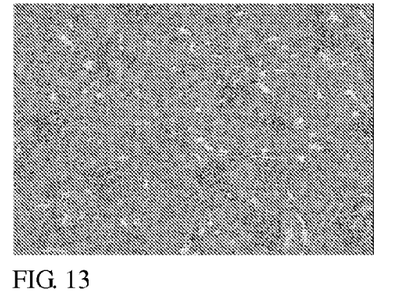
FIG. 13 shows liver tissue section of *Lactobacillus fermentum* SG-A95 prevention group (pLFBH) (200×).
Figure 14:
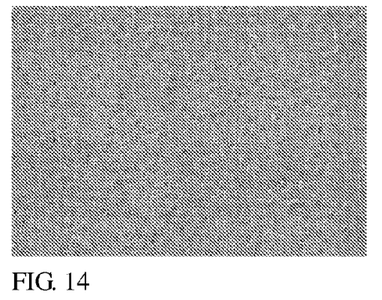
FIG. 14 shows liver tissue section of control group with tetracycline prevention treatment (pTC) (200×).
Figure 15:
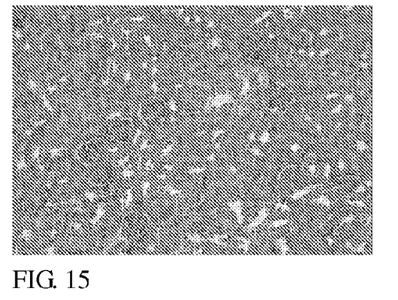
FIG. 15 shows kidney tissue section of control group with tetracycline prevention treatment (pTC) (200×).
Figure 16:
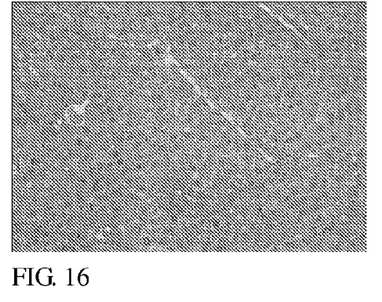
FIG. 16 shows liver tissue section of control group with no prevention treatment (distilled water) (pMT) (200×).
Figure 17:
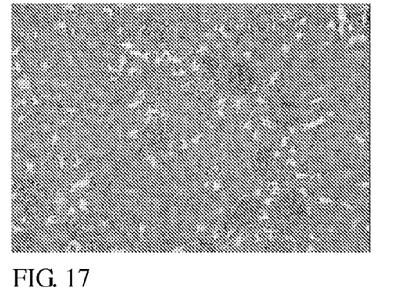
FIG. 17 shows kidney tissue section of control group with no prevention treatment (distilled water) (pMT) (200×).

SEQ ID NO: 1 of the present invention has significant difference as compared to the genetic material of known *Lactobacillus fermentum* (shown in FIG. 1). The API 50 CHL comparison revealed significant difference of *Lactobacillus fermentum* SG-A95 of the present invention against EU patent 0154549 disclosed strain AD0002 (deposit number FERM P-7539) as shown in Table 1.

TABLE 1

API 50 CHL comparison of *Lactobacillus fermentum* of the present invention and EU patent 0154549 revealed strain AD0002 (deposit number FERM P-7539).

| API 50 CHL | Sugar group | LF (*Lactobacillus fermentum* of the present invention) | EP0154549 (AD0002) (FERM P-7539) |
|---|---|---|---|
| 0 | Control | − | |
| 1 | Glycerol | − | |
| 2 | Erythritol | − | |
| 3 | D-Arabinose | − | + |
| 4 | L-Arabinose | − | |
| 5 | D-Ribose | + | + |
| 6 | D-Xylose | − | + |
| 7 | L-Xylose | − | |
| 8 | Adonitol | − | |
| 9 | β-Methyl-xyloside | − | |
| 10 | Galactose | + | + |
| 11 | D-Glucose | + | + |
| 12 | D-Fructose | + | |
| 13 | D-Mannose | − | − |
| 14 | L-Sorbose | − | |
| 15 | Rhamnose | − | |
| 16 | Dulcitol | − | |
| 17 | Inositol | − | |
| 18 | Mannitol | − | − |
| 19 | Sorbitol | − | − |
| 20 | α-Methyl-D-mannoside | − | |
| 21 | α-Methyl-D-glucoside | − | |
| 22 | N-Acetyl glucosamine | − | |
| 23 | Amygdaline | − | − |

TABLE 1-continued

API 50 CHL comparison of *Lactobacillus fermentum* of the present invention and EU patent 0154549 revealed strain AD0002 (deposit number FERM P-7539).

| API 50 CHL | Sugar group | LF (*Lactobacillus fermentum* of the present invention) | EP0154549 (AD0002) (FERM P-7539) |
|---|---|---|---|
| 24 | Arbutine | − | |
| 25 | Esculine | − | − |
| 26 | Salicine | − | − |
| 27 | Cellobiose | − | − |
| 28 | Maltose | + | + |
| 29 | Lactose | − | + |
| 30 | Melibiose | + | + |
| 31 | Saccharose | + | + |
| 32 | Trehalose | − | + |
| 33 | Inuline | − | |
| 34 | Melezitose | − | − |
| 35 | D-Raffinose | + | + |
| 36 | Amidon | − | |
| 37 | Glycogen | − | |
| 38 | Xylitol | − | |
| 39 | β-Gentiobiose | − | |
| 40 | D-Turanose | − | |
| 41 | D-Lyxose | − | |
| 42 | D-Tagatose | − | |
| 43 | D-Fucose | − | |
| 44 | L-Fucose | − | |
| 45 | D-Arabitol | − | |
| 46 | L-Arabitol | − | |
| 47 | Gluconate | − | |
| 48 | 2 keto-gluconate | − | |
| 49 | 5 keto-gluconate | − | |

The subject in the present invention is mammal. In a preferred embodiment, the subject is human.

The in vitro or in vivo study have shown that commonly seen periodontal bacteria, such as *Streptococcus mutans*, *Streptococcus sanguis*, *Porphyromonas gingivalis* and *Actinomyces viscosus*, are affected by live *Lactobacillus fermentum* or its fermentation product to the level of seizing growth or even death. Based on the characteristics of *Lactobacillus fermentum* inhibiting oral bacteria growth, *Lactobacillus fermentum* could be applied to prevent or treat the oral bacterial diseases as follows:

1. *Porphyromonas gingivalis* related diseases: periodontal disease, osteoporosis, cavernous sinus thrombophlebitis, periodontitis, cardiovascular disease, infective endocarditis, diabetes, respiratory disease, atherosclerosis, coronary heart disease, stroke, and rheumatoid arthritis.

2. *Streptococcus sanguis* related diseases: cavity, infective endocarditis, acute septic arthritis, and cardiovascular disease.

3. *Streptococcus mutans* related diseases: cavity and infective endocarditis.

4. *Actinomyces viscosus* related diseases: periodontitis.

The present invention discloses live *Lactobacillus fermentum* SG-A95 itself can inhibit bacteria growth. For practical application, *Lactobacillus fermentum* SG-A95 can be applied to directly spread on the oral cavity. It is also possible to freeze or dry bacteria of the present invention without compromising the reconstitute activity in the mouth, and then to formulate into tablet, spray, solution, additive of food, pharmaceutical or oral hygiene for application. Any method which does not compromise live *Lactobacillus fermentum*

SG-A95 bacterial inhibition ability can be the applicable method for the present invention.

*Lactobacillus fermentum* SG-A95 fermentation product discloses in the present invention is the product after fermentation of *Lactobacillus fermentum* SG-A95 via culture medium containing appropriate ingredients for Lactobacillus fermentum SG-A95 growth. The major ingredients of the medium include glucose, peptone, meat extract, yeast extract, salt and etc. The bacteria inhibition activity of Lactobacillus fermentum SG-A95 fermentation product is not affected by dialyzing; for example, dialyze by SPECTRA/POR® dialysis membrane (MWCO:3500). It demonstrates that the bacteria inhibition activity is not completely relying on the live *Lactobacillus fermentum*, but the metabolites during fermentation process. Therefore, the present invention discloses oral health care composition with active ingredient of *Lactobacillus fermentum* SG-A95 can include only *Lactobacillus fermentum* fermentation product after removing the live *Lactobacillus fermentum*.

For practical application, *Lactobacillus fermentum* SG-A95 fermentation product can be applied directly by spreading on the oral cavity, provided in the form of tablet, spray, solution or additive of food, pharmaceutical or oral hygiene for application. Any method which does not compromise the bacterial inhibition activity of *Lactobacillus fermentum* SG-A95 fermentation product can be the applicable method for the present invention.

Example

The present invention reveals a health care composition for preventing or treating oral bacterial diseases wherein the active ingredient comprises *Lactobacillus fermentum* SG-A95 or its fermentation product. In vitro or in vivo study in the present invention demonstrated therapeutic effects of said bacteria or its fermentation products against periodontal diseases.

1. In Vitro Study

*Lactobacillus fermentum* SG-A95 was cultured in liquid medium. MRS medium was used in this embodiment. The bacteria were cultured at 30~37° C. for 15~24 hours. The fermentation broth was concentrated into 30-fold of original concentration and dialyzed with SPECTRA/POR® Dialysis Membrane (MWCO:3500, Spectrum Laboratories Inc, CA) for 48 hours. Lactobacillus fermentum SG-A95 and concentrate fermentation product were diluted into various concentrations according to experimental requirements. Disc agar diffusion test, broth dilution method, and co-cultivation test of *Lactobacillus fermentum* SG-A95 with *Streptococcus mutans* (ATCC 25175), *Streptococcus sanguis* (ATCC 49295), *Porphyromonas gingivalis* (ATCC 33277), and *Actinomyces viscosus* (ATCC 15987) were separately performed to understand the inhibition of pathogen growth. Above four pathogens strains were purchased from Bioresource Collection and Research Center of Food Industry Research and Development Institute in Taiwan or ATCC.

MRS medium was usually used for *Lactobacillus fermentum* cultivation, and its major ingredients included glucose, peptone, meat extract, yeast extract, salt, and etc.

(1) Disc Agar Diffusion Test

*Streptococcus mutans, Streptococcus sanguis, Porphyromonas gingivalis* and *Actinomyces viscosus* were cultured to 0.5 McFarland turbidity. Dip bacteria culture with sterile cotton swab for 3 seconds, and each bacteria was smeared on agar plates in three directions to evenly distribute the incoculum. After dialyzing 30-fold fermentation product of *Lactobacillus fermentum* SG-A95, adjust concentrate to 4-fold concentrate (LFP4), 2-fold concentrate (LFP2) and 1-fold (LFP1) (unconcentrated fermentation broth). The live *Lactobacillus fermentum* SG-A95 was dilute into $1 \times 10^9$ (LFBL), $2 \times 10^9$ (LFBM) and $5 \times 10^9$ (LFBH). 6 mm diameter autoclaved paper discs were soaked in different concentrations of *Lactobacillus fermentum* SG-A95 fermentation product or live *Lactobacillus fermentum* SG-A95 suspension for 3 seconds, the paper discs were placed on the agar plates, the plates were incubated in a 37 anaerobic incubator for 24 hours, and the sizes of inhibition zones were measured.

(2) Broth Dilution Method

After dialyzing 30-fold fermentation product of *Lactobacillus fermentum* SG-A95, adjust the concentration of fermentation product into 4-fold concentrate (LFP4), 2-fold concentrate (LFP2) and 1-fold (LFP1) (unconcentrated fermentation broth). Each of *Streptococcus mutans, Streptococcus sanguis, Porphyromonas gingivalis* and *Actinomyces viscosus* was cultured in sterile BHI broth to 0.5 McFarland turbidity, 50 µL of bacteria suspension was add into test tubes, and cultured in a 37 anaerobic incubator for 48 hours. Plate counts were performed to calculate bacteria colony number for estimating bacterial inhibition concentrations of samples.

(3) Co-Culture Test of *Lactobacillus fermentum* SG-A95 and Pathogens

Live *Lactobacillus fermentum* SG-A95 and *Streptococcus mutans, Streptococcus sanguis* and *Porphyromonas gingivalis* was placed into test tubes simultaneously and co-cultured at 37. Samples were taken at different time points. Plate counts were performed to calculate bacteria colony number to investigate pathogen growth inhibition of samples.

2. In Vivo Study

This trial included treatment groups and control groups. The treatment group of *Lactobacillus fermentum* SG-A95 were divided into 6 groups as follows: 3 groups of dialyzed *Lactobacillus fermentum* SG-A95 fermentation product concentrate such as 4-fold, 2-fold, and 1-fold (unconcentrated fermentation broth) and 3 groups of *Lactobacillus fermentum* SG-A95 in various numbers of bacteria such as $1 \times 10^9$, $2 \times 10^9$ and $5 \times 10^9$. Two control groups were treated with 0.267 mg/mL of tetracycline and distilled water.

(1) Evaluation of Preventive Effect for Animal Periodontal Disease

Twelve of 8-week-old female Balb/c mice were selected for each group (Table 2). The mice were administered with various concentrations of *Lactobacillus fermentum* SG-A95 fermentation product or live *Lactobacillus fermentum* SG-A95, and 1 mL of 0.267 mg/mL tetracyccline or distilled water separately. Their mandibular anterior teeth were tied with a ligature wire and inoculate periodontal pathogen *Streptococcus mutans* in gum tissue as an animal model of artificially induced periodontal disease. Their pathological symptoms were observed and recorded until sacrificing all animals. Until the control group (feeding with distilled water, mock-treated group) showing gum swelling and dental plaque appearance diagnosed by chief dentists, the ligature wire was removed and inoculation of dental pathogen was stopped. At day 4, 8, 12, and 16 after wire removal, mice periodontal pocket depth was examined, 3 mice from each group were killed for blood sampling and samples were collected for histological analysis.

TABLE 2

Prevention groups of animal study (Note: The tetracycline dose of human is 1000 mg/75 kg body weight/day. The estimated dose of mice is about 0.267 mg/20 g body weight/day).

|  |  | Applied dose (/mL) | Group numbers |
|---|---|---|---|
| pLFP1 | Lactobacillus | 1 X | 8 |
| pLFP2 | fermentum SG-A95 | 2 X concentrate |  |
| pLFP4 | fermentation product | 4 X concentrate |  |
| pLFBL | Live Lactobacillus | $1 \times 10^9$ |  |
| pLFBM | fermentum SG-A95 | $2 \times 10^9$ |  |
| pLFBH | (CFU) | $5 \times 10^9$ |  |
| pTC | Tetracycline | 0.267 mg |  |
| pMT | Distilled water (mock treatment) |  |  |

(2) Evaluation of Therapeutic Effect for Animal Periodontal Disease

Twelve of 8-week-old female Balb/c mice were selected for each group (Table 3). Until the control group showing gum swelling and dental plaque appearance, their mandibular anterior teeth were tied with the ligature wire and inoculated periodontal pathogen *Streptococcus mutans* in gum tissue as an animal model of artificially induced periodontal disease. After diagnosis of diseased tissue by chief dentists, they were administered different concentrations of *Lactobacillus fermentum* SG-A95 fermentation product, live *Lactobacillus fermentum* SG-A95, 1 mL of 0.267 mg/mL tetracycline or distill water every day. The symptoms were recorded. The wire was removed at the beginning of the treatment and stop periodontal pathogen inoculation. At day 4, 8, 12, and 16 after wire removal, mice periodontal pocket depth was examined. 3 mice from each group were killed for blood sampling and histological analysis.

TABLE 3

Animal test treatment group

|  |  | Applied dose (/mL) | Group numbers |
|---|---|---|---|
| tLFP1 | Lactobacillus fermentum | 1 X | 8 |
| tLFP2 | SG-A95 fermentation | 2 X concentrate |  |
| tLFP4 | product | 4 X concentrate |  |
| tLFBL | Live Lactobacillus | $1 \times 10^9$ |  |

TABLE 3-continued

Animal test treatment group

|  |  | Applied dose (/mL) | Group numbers |
|---|---|---|---|
| tLFBM | fermentum SG-A95 (CFU) | $2 \times 10^9$ |  |
| tLFBH |  | $5 \times 10^9$ |  |
| tTC | Tetracycline | 0.267 mg |  |
| tMT | Distilled water (mock treatment) |  |  |

(3) Improvement Percentage of Periodontal Pocket Depth

Control group was used as a standard to examine subjects from each group by Mann-Whitney test. Subjects with significant difference were defined as improving subjects (number of improving subject/number of total subject in group)×100%=improvement percentage of periodontal pocket depth.

(4) Clinical Pathological and Blood Biochemical Analysis

The mice were killed. Blood samples from carotid artery were centrifuged at 3000 rpm for 10 minutes at 4. Serum in the supernatant was taken. Its ALT, AST, Creatinine and BUN biochemical indicator were analysis with an automated biochemical analyzer. important target organs were collected (liver, kidney), and fixed with 10% formalin solution. After making parafilm section, H.E. staining was performed for pathological observation.

3. Statistic Analysis

Experimental data was shown as mean±S.D. The statistical variation of treatment groups and control groups of mice periodontal pocket was performed by One-Way ANOVA and Dunnett multiple post hoc comparison in longitudinal study, and by One-Way ANOVA and LSD multiple post hoc comparison in cross-sectional study. Besides, Mann-Whitney test was used to examine the number of periodontal pocket improving individuals. The statistical significance level of p value was 0.05.

Results

1. In Vitro Study (1) Disc Agar Diffusion Test

Table 4 showed the inhibition effect of disc agar diffusion test. The diameter of sterile paper disc was 6 mm. The positive bacterial inhibition effect was determined by over 6 mm bacterial inhibition zone. Otherwise, it was defined as negative bacterial inhibition effect. The cultural condition was under the temperature of 37 for 24 hours. The paper disc was used in control group containing tetracycline. The inhibition zone value was shown as mean±S.D. (n=3).

TABLE 4

| Bacterial inhibition effect of disc agar diffusion test | | | | |
|---|---|---|---|---|
|  | *Actinomyces viscosus* | *Porphyromonas gingivalis* | *Streptococcus mutans* | *Streptococcus sanguis* |
| LFP1 | — | — | — | — |
| LFP2 | 7.0 ± 1.0 | 9.2 ± 1.0 | 7.6 ± 0.9 | 7.7 ± 1.0 |
| LFP4 | 9.8 ± 1.1 | 9.7 ± 0.6 | 13.2 ± 1.2 | 12.4 ± 1.2 |
| LFBL | 10 ± 1.0 | 11 ± 1.0 | 9 ± 0.5 | 9 ± 0.5 |
| LFBM | 10 ± 1.0 | 10 ± 1.0 | 9 ± 0.5 | 9 ± 0.5 |

TABLE 4-continued

Bacterial inhibition effect of disc agar diffusion test

|  | Actinomyces viscosus | Porphyromonas gingivalis | Streptococcus mutans | Streptococcus sanguis |
|---|---|---|---|---|
| LFBH | 10 ± 1.0 | 10 ± 1.0 | 9 ± 0.5 | 9 ± 0.5 |
| tetracycline | 48.2 ± 2.4 | 33.4 ± 2.2 | 29.7 ± 2.0 | 25.9 ± 1.2 |

Table 4 showed that *Lactobacillus fermentum* SG-A95 fermentation product of over 2-fold concentrate and live *Lactobacillus fermentum* produced inhibition zone against these four pathogens, such as *Actinomyces viscosus, Porphyromonas gingivalis, Streptococcus mutans* and *Streptococcus sanguis*.

(2) Broth Dilution Method

TABLE 5

The minimal bacteria inhibition concentration and inhibition percentage (100% − (experimental group ÷ control group) × 100%).

|  | *Actinomyces viscosus* | | *Porphyromonas gingivalis* | | *Streptococcus mutans* | | *Streptococcus sanguis* | |
|---|---|---|---|---|---|---|---|---|
|  | CFU/ml | Inhibition | CFU/ml | Inhibition | CFU/ml | Inhibition | CFU/ml | Inhibition |
| LFP4 | $1.11 \times 10^{10}$ | 46.4% | $2.83 \times 10^9$ | 67.9% | $2.72 \times 10^{10}$ | 21.4% | $4.61 \times 10^{10}$ | 35.2% |
| LFP2 | $1.73 \times 10^{10}$ | 16.5% | $4.77 \times 10^9$ | 45.9% | $3.50 \times 10^{10}$ | 0% | $6.28 \times 10^{10}$ | 11.7% |
| LFP1 | $2.27 \times 10^{10}$ | 0% | $8.54 \times 10^9$ | 3.1% | $3.46 \times 10^{10}$ | 0% | $6.89 \times 10^{10}$ | 3.1% |
| control | $2.07 \times 10^{10}$ | — | $8.81 \times 10^9$ | — | $3.46 \times 10^{10}$ | — | $7.11 \times 10^{10}$ | — |

Table 5 showed different inhibition effects of *Lactobacillus fermentum* SG-A95 fermentation product after treating periodontal pathogens 48 hours at various concentrations. In general, high concentration of *Lactobacillus fermentum* SG-A95 product produced better inhibition effect. For periodontal pathogens, *Lactobacillus fermentum* SG-A95 fermentation product showed the most significant inhibition effect on *Porphyromonas gingivalis* in a dose-dependent manner. The second significant inhibition effect was against *Actinomyces viscosus*. The *Lactobacillus fermentum* of over 2-fold concentrate illustrated the inhibition effect against these four pathogens.

(3) Co-Culture Test of *Lactobacillus Fermentum* SG-A95 and Pathogens

TABLE 6

Inhibition of pathogen growth by co-culture of live *Lactobacillus fermentum* SG-A95 (LF) and *Streptococcus mutans*

| Culture time | *Streptococcus mutans* | | | |
|---|---|---|---|---|
| (hour) | LF($10^7$) | LF($10^8$) | LF($10^9$) | control |
| 0 | $5.0 \times 10^7$ | $5.0 \times 10^7$ | $5.0 \times 10^7$ | $5.0 \times 10^7$ |
| 4 | $1.7 \times 10^8$ | $1.5 \times 10^8$ | $3.2 \times 10^7$ | $4.4 \times 10^8$ |
| 8 | $2.0 \times 10^8$ | $1.2 \times 10^8$ | $1.0 \times 10^7$ | $1.5 \times 10^9$ |
| 24 | $3.9 \times 10^6$ | $1.6 \times 10^5$ | $2.8 \times 10^6$ | $1.3 \times 10^9$ |
| 32 | $4.6 \times 10^2$ | $6.5 \times 10^3$ | $1.1 \times 10^5$ | $1.0 \times 10^7$ |
| 48 | 0 | 0 | 0 | $1.0 \times 10^7$ |

Table 6 showed co-culture of live *Lactobacillus fermentum* SG-A95 and *Streptococcus mutans*. There was no *Streptococcus mutans* presented in groups of under low ($10^7$), median ($10^8$) or high bacteria counts ($10^9$) after 48 hours of co-culture. It demonstrated its growth inhibition effect against *Streptococcus mutans*.

TABLE 7

Inhibition of pathogen growth by co-culture live *Lactobacillus fermentum* SG-A95 and *Streptococcus sanguis*.

| Culture time | *Streptococcus sanguis* | | | |
|---|---|---|---|---|
| (hour) | LF($10^7$) | LF($10^8$) | LF($10^9$) | control |
| 0 | $3.0 \times 10^7$ | $5.0 \times 10^7$ | $5.0 \times 10^7$ | $5.0 \times 10^7$ |
| 2 | $5.1 \times 10^6$ | $7.9 \times 10^6$ | $8.3 \times 10^5$ | $5.3 \times 10^7$ |
| 4 | $1.9 \times 10^6$ | $4.0 \times 10^6$ | $3.1 \times 10^5$ | $7.6 \times 10^7$ |
| 6 | $7.6 \times 10^5$ | $6.5 \times 10^5$ | $5.7 \times 10^3$ | $9.1 \times 10^7$ |
| 8 | $1.4 \times 10^5$ | $1.9 \times 10^5$ | $4.8 \times 10^1$ | $1.0 \times 10^8$ |
| 10 | $7.3 \times 10^4$ | $6.2 \times 10^4$ | 0 | $3.2 \times 10^8$ |
| 12 | $4.5 \times 10^3$ | $3.3 \times 10^3$ | 0 | $4.3 \times 10^8$ |
| 14 | 0 | 0 | 0 | $7.4 \times 10^8$ |

Table 7 showed co-culture of live *Lactobacillus fermentum* SG-A95 and *Streptococcus sanguis*. After 10 hours of co-culture, there was no *Streptococcus sanguis* presented in high bacteria counts group ($10^9$). After 14 hours of co-culture, there was no *Streptococcus sanguis* presented in median ($10^8$) and low bacteria counts groups ($10^7$). It demonstrated its growth inhibition effect against *Streptococcus sanguis*.

TABLE 8

Inhibition of pathogen growth by co-culture of live *Lactobacillus fermentum* SG-A95 and *Porphyromonas gingivalis*.

| Culture time (hour) | *Porphyromonas gingivalis* | | | |
|---|---|---|---|---|
|  | LF($10^7$) | LF($10^8$) | LF($10^9$) | Control |
| 0 | $2.4 \times 10^7$ | $5.0 \times 10^7$ | $5.0 \times 10^7$ | $5.0 \times 10^7$ |
| 2 | $4.0 \times 10^7$ | $1.2 \times 10^8$ | $9.1 \times 10^8$ | $5.2 \times 10^7$ |
| 4 | $1.2 \times 10^8$ | $3.5 \times 10^8$ | $6.0 \times 10^2$ | $7.3 \times 10^7$ |
| 6 | $8.6 \times 10^7$ | $4.5 \times 10^3$ | 0 | $1.3 \times 10^8$ |
| 8 | $3.5 \times 10^7$ | 0 | 0 | $4.2 \times 10^8$ |
| 10 | $3.8 \times 10^6$ | 0 | 0 | $5.5 \times 10^8$ |

TABLE 8-continued

Inhibition of pathogen growth by co-culture of live
Lactobacillus fermentum SG-A95 and Porphyromonas gingivalis.

| Culture | Porphyromonas gingivalis | | | |
|---|---|---|---|---|
| time (hour) | LF($10^7$) | LF($10^8$) | LF($10^9$) | Control |
| 12 | $5.5 \times 10^3$ | 0 | 0 | $6.0 \times 10^8$ |
| 14 | 0 | 0 | 0 | $5.5 \times 10^8$ |

Table 8 showed co-culture of live *Lactobacillus fermentum* SG-A95 and *Porphyromonas gingivalis*. After 6 hours of co-culture, there was no *Porphyromonas gingivalis* presented in high bacteria counts group ($10^9$). Co-culture for 8 hours of median bacteria counts group ($10^8$) and 14 hours cultivation of low bacteria counts group ($10^7$) showed the same effect. It demonstrated its growth inhibition effect against *Porphyromonas gingivalis*.

TABLE 9

Comparison of the mice periodontal pocket depth (mm) of *Lactobacillus fermentum* SG-A95 prevention group (pLF) (One-Way ANOVA and Dunnett multiple post hoc comparison) with control group (pMT) at different time points (*$p < 0.05$; **$p < 0.01$).

| | Day 4 | Day 8 | Day 12 | Day 16 |
|---|---|---|---|---|
| pLFP1 | 0.79 ± 0.44** | 0.75 ± 0.27** | 0.42 ± 0.35** | 0.35 ± 0.21** |
| pLFP2 | 0.77 ± 0.31** | 1.21 ± 0.64** | 0.80 ± 0.81** | 1.25 ± 0.35** |
| pLFP4 | 1.04 ± 0.66** | 0.79 ± 0.26** | 0.48 ± 0.29** | 0.30 ± 0.17** |
| pLFBL | 1.33 ± 0.44** | 1.17 ± 0.55** | 0.83 ± 0.41** | 0.67 ± 0.29** |
| pLFBM | 1.08 ± 0.67** | 0.83 ± 0.43** | 0.57 ± 0.36** | 0.33 ± 0.15** |
| pLFBH | 1.00 ± 0.50** | 0.84 ± 0.41** | 0.38 ± 0.16** | 0.25 ± 0.70** |
| pTC | 0.84 ± 0.50** | 0.70 ± 0.34** | 0.56 ± 0.26** | 0.49 ± 0.25** |
| pMT | 2.22 ± 1.07 | 2.16 ± 1.25 | 2.75 ± 1.32 | 2.21 ± 0.64 |

Effects on periodontal pocket depth of prevention groups treated with various concentrations of *Lactobacillus fermentum* SG-A95 fermentation product and live bacteria were shown in table 9. Significant difference was observed in all groups against control group of feeding distilled water (pMT) at all time points. Significant difference was also observed in prevention control group feed with tetracycline (pTC) at all time points.

Inter group of various concentration in treated prevention groups of *Lactobacillus fermentum* SG-A95 fermentation 2. In Vivo Study (1) Evaluation of the Prevention Effect for Animal Periodontal Disease product and live bacteria at various time points was compared and shown in Table 10. Significant difference of periodontal pocket improvement level was shown in 4-fold concentration group (pLFP4), high bacteria counts group (pLFBH) and tetracycline group (pTC) at day 12 and 16.

TABLE 10

Comparison of the mice periodontal pocket depth (mm) in *Lactobacillus fermentum* SG-A95 prevention group (pLF) with day 4 at various time points and various concentration (One-Way ANOVA and LSD multiple post hoc comparison; *$p < 0.05$; **$p < 0.01$).

| | pLFP1 | pLFP2 | pLFP4 | pLFBL | pLFBM | pLFBH | pTC | pMT |
|---|---|---|---|---|---|---|---|---|
| Day 4 | 0.79 ± 0.44 | 0.77 ± 0.31 | 1.04 ± 0.66 | 1.33 ± 0.45 | 1.08 ± 0.67 | 1.00 ± 0.50 | 0.84 ± 0.50 | 2.22 ± 1.07 |
| Day 8 | 0.75 ± 0.27 | 1.21 ± 0.64 | 0.79 ± 0.26 | 1.17 ± 0.55 | 0.83 ± 0.43 | 0.84 ± 0.41 | 0.70 ± 0.34 | 2.16 ± 1.25 |
| Day 12 | 0.42 ± 0.35 | 0.80 ± 0.81 | 0.48 ± 0.29* | 0.83 ± 0.43 | 0.57 ± 0.36 | 0.38 ± 0.16* | 0.56 ± 0.26* | 2.75 ± 1.32 |
| Day 16 | 0.35 ± 0.21 | 1.25 ± 0.35 | 0.30 ± 0.17* | 0.67 ± 0.29 | 0.33 ± 0.15 | 0.25 ± 0.70* | 0.49 ± 0.25* | 2.21 ± 0.64 |

(2) Evaluation of Therapeutic Effect for Animal Periodontal Disease

TABLE 11

Comparison of the mice periodontal pocket depth (mm) in *Lactobacillus fermentum* SG-A95 treatment groups (tLF) against control group (tMT) at different time points (One-Way ANOVA and Dunnett multiple post hoc comparison; *$p < 0.05$; **$p < 0.01$).

| | Day 4 | Day 8 | Day 12 | Day 16 |
|---|---|---|---|---|
| tLFP1 | 0.71 ± 0.38** | 1.19 ± 0.62 | 1.00 ± 0.61** | 0.75 ± 0.35* |
| tLFP2 | 1.23 ± 0.66** | 1.78 ± 0.71 | 0.92 ± 0.20** | 0.73 ± 0.46* |
| tLFP4 | 1.04 ± 0.58** | 0.83 ± 0.50* | 0.67 ± 0.41** | 0.30 ± 0.17** |
| tLFBL | 1.33 ± 0.62** | 1.28 ± 1.15 | 0.68 ± 0.72** | 0.57 ± 0.40** |
| tLFBM | 1.96 ± 0.96 | 1.75 ± 0.80 | 1.00 ± 0.50** | 1.50 ± 0.71 |
| tLFBH | 1.42 ± 0.79* | 0.83 ± 0.43* | 0.33 ± 0.31** | 0.30 ± 0.17** |
| tTC | 1.05 ± 0.64** | 0.89 ± 0.44** | 0.63 ± 0.37** | 0.48 ± 0.33** |
| tMT | 2.10 ± 0.63 | 1.91 ± 0.89 | 2.10 ± 0.97 | 2.00 ± 0.92 |

Effects on periodontal pocket depth of treatment groups treated with various concentrations of *Lactobacillus fermentum* SG-A95 fermentation product and live bacteria was shown in Table 11. The significant difference was shown in all groups at various time points. When comparing groups at various time points to control group (tMT), the significant difference was shown in 4-fold concentration group (tLFP4), high bacteria counts group (tLFBH) and tetracycline group (tTC) in each time point. Groups feeding 1-fold and 2-fold concentration of fermentation product (tLFP1 and tLFP2) and low bacteria counts broup (tLFBL) showed significant difference in all time points except day 8. The significant difference was showed in group feeding with median bacteria counts (tLFBM) only at day 12.

TABLE 12

Comparison of the mice periodontal pocket depth (mm) in *Lactobacillus fermentum* SG-A95 treatment groups (tLF) with day 4 at various time points and different concentrations (One-Way ANOVA and LSD multiple post hoc comparison; *$p < 0.05$; **$p < 0.01$).

|  | pLFP1 | pLFP2 | pLFP4 | pLFBL | pLFBM | pLFBH | pTC | pMT |
|---|---|---|---|---|---|---|---|---|
| Day 4 | 0.71 ± 0.38 | 1.23 ± 0.66 | 1.04 ± 0.58 | 1.33 ± 0.63 | 1.96 ± 0.96 | 1.42 ± 0.79 | 1.05 ± 0.64 | 2.10 ± 0.63 |
| Day 8 | 1.19 ± 0.62 | 1.78 ± 0.71* | 0.83 ± 0.50 | 1.28 ± 1.15 | 1.75 ± 0.80 | 0.83 ± 0.43* | 0.89 ± 0.44 | 1.91 ± 0.89 |
| Day 12 | 1.00 ± 0.61 | 0.92 ± 0.20 | 0.67 ± 0.41 | 0.68 ± 0.72 | 1.00 ± 0.50 | 0.33 ± 0.31** | 0.63 ± 0.37** | 2.10 ± 0.97 |
| Day 16 | 0.75 ± 0.35 | 0.73 ± 0.46 | 0.30 ± 0.17 | 0.57 ± 0.40 | 1.50 ± 0.71 | 0.30 ± 0.17** | 0.61 ± 0.34** | 2.00 ± 0.92 |

Inter group comparison of treatment groups feeding with *Lactobacillus fermentum* SG-A95 fermentation product and live bacteria against various time points was shown in Table 12. The significant difference was shown in high bacteria counts group (tLFBH) at day 8, 12 and 16 against day 4. The significant difference was shown in tetracycline group (tTC) at day 12 and 16.

(3) Improvement Percentage of Periodontal Pocket Depth

TABLE 13

The periodontal pocket improvement percentage of *Lactobacillus fermentum* SG-A95 prevention groups (pLF) showed significant difference against no-treatment control group in prevention control (pMT) by Mann-Whitney test ($p < 0.05$, percentage of improving individual).

|  | Day 4 | Day 8 | Day 12 | Day 16 |
|---|---|---|---|---|
| pLFP1 | 64% | 50% | 80% | 100% |
| pLFP2 | 40% | 29% | 75% | 50% |
| pLFP4 | 42% | 33% | 67% | 67% |
| pLFBL | 8% | 11% | 33% | 67% |
| pLFBM | 42% | 22% | 67% | 100% |
| pLFBH | 36% | 25% | 80% | 100% |
| pTC | 62% | 50% | 71% | 100% |
| pMT | — | — | — | — |

The periodontal pocket depth improvement percentages in *Lactobacillus fermentum* SG-A95 prevention groups reached 100% at day 16, except 2-fold and 4-fold concentration groups and low bacterias count group (pLFP2, pLFP4 and pLFBL).

TABLE 14

The periodontal pocket improvement percentage of *Lactobacillus fermentum* SG-A95 treatment groups (tLF) showed significant difference against no-treatment control group (tMT) by Mann-Whitney test ($p < 0.05$, percentage of improving individual).

|  | Day 4 | Day 8 | Day 12 | Day 16 |
|---|---|---|---|---|
| tLFP1 | 58% | 22% | 40% | 50% |
| tLFP2 | 17% | 0 | 17% | 33% |
| tLFP4 | 42% | 22% | 83% | 100% |
| tLFBL | 8% | 44% | 67% | 67% |
| tLFBM | 9% | 13% | 40% | 0 |

TABLE 14-continued

The periodontal pocket improvement percentage of *Lactobacillus fermentum* SG-A95 treatment groups (tLF) showed significant difference against no-treatment control group (tMT) by Mann-Whitney test ($p < 0.05$, percentage of improving individual).

|  | Day 4 | Day 8 | Day 12 | Day 16 |
|---|---|---|---|---|
| tLFBH | 17% | 33% | 83% | 100% |
| tTC | 30% | 20% | 47% | 33% |
| tMT | — | — | — | — |

*Lactobacillus fermentum* SG-A95 treatment groups showed improvement percentage of 33%~100% at day 16 except median bacteria count group.

(4) Clinical Pathological Analysis

The liver and kidney tissue section of groups feeding SG-A95 fermentation product or highest concentration of live bacteria at day 16 (FIG. 2 to FIG. 5 and FIG. 10 to FIG. 13) revealed no significant appearance of toxic effect and no inflammatory cell infiltration as compared to no-treatment control groups (tMT or pMT) (FIG. 6 to FIG. 9 and FIG. 14 to FIG. 17).

Conclusion

In vitro study of disc agar diffusion test revealed that *Lactobacillus fermentum* SG-A95 fermentation product of more than 2-fold concentrate formed inhibition zones against these four pathogens. Live *Lactobacillus fermentum* SG-A95 at $1 \times 10^9$ cfu/mL(LFBL), $2 \times 10^9$ cfu/mL(LFBM) or $5 \times 10^9$ cfu/mL(LFBH) all showed 9 to 10 mm of inhibition zones against these four periodontal pathogens, such as *Actinomyces visco-* sus, *Porphyromonas gingivalis*, *Streptococcus mutans*, and *Streptococcus sanguis*. Broth dilution method test revealed that various concentrations of *Lactobacillus fermentum* SG-A95 fermentation product had different inhibition effects on periodontal pathogens. Co-culture data showed that live *Lactobacillus fermentum* SG-A95 had the maximal inhibition effect on *Porphyromonas gingivalis*. It also inhibited the growth of *Streptococcus mutans* and *Streptococcus sanguis*. High bacteria counts groups showed better inhibition effect.

Animals of treatment groups feeding with *Lactobacillus fermentum* SG-A95 fermentation product or the high bacteria counts were sacrificed at day 16 for pathological section of liver and kidney tissues. The results showed no significant difference of appearance of toxic effect representing its high safety.

In combination of in vitro and in vivo studies, it showed that *Lactobacillus fermentum* SG-A95 fermentation product and live bacteria prevented periodontal disease and improved periodontal inflammation condition.

SEQUENCE LISTING

<160> NUMBER OF SEQ ID NOS: 1

<210> SEQ ID NO 1
<211> LENGTH: 1113
<212> TYPE: DNA
<213> ORGANISM: Lactobacillus fermentum

<400> SEQUENCE: 1

```
ggacgtgcga gtgctataca tgcaagtcga acgcgttggc ccaattgatt gatggtgctt      60
gcacctgatt gattttggtc gccaacgagt ggcggacggg tgagtaacac gtaggtaacc     120
tgcccagaag cggggacaa catttggaaa cagatgctaa taccgcataa cagcgttgtt      180
cgcatgaaca acgcttaaaa gatggcttct cgctatcact tctggatgga cctgcggtgc     240
attagcttgt tggtgggta acggcctacc aaggcgatga tgcatagccg agttgagaga     300
ctgatcggcc acaatgggac tgagacacgg cccatactcc tacgggaggc agcagtaggg     360
aatcttccac aatgggcgca agcctgatgg agcaacaccg cgtgagtgaa gaagggtttc     420
ggctcgtaaa gctctgttgt taaagaagaa cacgtatgag agtaactgtt catacgttga     480
cggtatttaa ccagaaagtc acggctaact acgtgccagc agccgcggta atacgtaggt     540
ggcaagcgtt atccggattt attgggcgta aagagagtgc aggcggtttt ctaagtctga     600
tgtgaaagcc ttcggcttaa ccggagaagt gcatcggaaa ctggataact tgagtgcaga     660
agagggtagt ggaactccat gtgtagcggt ggaatgcgta gatatatgga agaacaccag     720
tggcgaaggc ggctacctgg tctgcaactg acgctgagac tcgaaagcat gggtagcgaa     780
caggattaga taccctggta gtccatgccg taaacgatga gtgctaggtg ttggagggtt     840
tccgcccttc agtgcccgga gctaacgcat taagcactcc gcctggggag tacgaccgca     900
aggttgaaac tcaaaggaat tgacggggcc cgcacaagcg gtggagcatg tggtttaatt     960
cgaagctacg cgagacctta ccagtctgac atcttgcgca accctagaga tagggcgttc    1020
cttcgggacg catgacagtg tgcatggtcg tcgtcagctc gtgtcgtgag atgttgggtt    1080
agtcccgcaa cgagcgcacc cctcgtttac tag                                  1113
```

In vivo study of periodontal disease animal model showed better preventive effect than therapeutic effect of *Lactobacillus fermentum* SG-A95 fermentation product and live bacteria on periodontal status improvement. For preventive effect, various feeding concentrations showed significant improvement on periodontal pocket depth in all treatment groups at various time points against the control (pMT). For therapeutic effect, fermentation product of 4-fold concentrate group (tLFP4) and high bacteria counts group (tLFBH) showed the best performance.

What is claim is:

1. An isolated strain of *Lactobacillus fermentum* SG-A95 with deposit number of CGMCC NO. 3248.

2. The strain of claim 1, wherein the isolated strain of *Lactobacillus fermentum* SG-A95 comprises nucleotide sequences of SEQ ID NO:1.

3. A health care composition for improving oral bacteria population, which comprises the isolated strain of *Lactobacillus fermentum* SG-A95 of claim 1.

4. The health care composition of claim 3, wherein the isolated strain of *Lactobacillus fermentum* SG-A95 is live bacterium.

5. The health care composition of claim 3, which is used for inhibiting growth of oral periodontal bacteria in a subject.

6. The health care composition of claim 5, wherein the periodontal bacteria comprises *Streptococcus mutans, Streptococcus sanguis, Porphyromonas gingivalis* or *Actinomyces viscosus*.

7. The health care composition of claim 5, wherein the subject is mammal.

8. The health care composition of claim 3, which is in the form of tablet, spray, solution or additives of food, pharmaceuticals or oral hygiene product.

* * * * *